US011299727B2

(12) United States Patent
Sakai et al.

(10) Patent No.: US 11,299,727 B2
(45) Date of Patent: Apr. 12, 2022

(54) SYSTEM FOR ANALYZING SINGLE CELL

(71) Applicant: Hitachi, Ltd., Tokyo (JP)

(72) Inventors: Tomoyuki Sakai, Tokyo (JP); Masataka Shirai, Tokyo (JP)

(73) Assignee: HITACHI, LTD., Tokyo (JP)

( * ) Notice: Subject to any disclaimer, the term of this patent is extended or adjusted under 35 U.S.C. 154(b) by 200 days.

(21) Appl. No.: 16/329,682

(22) PCT Filed: Mar. 6, 2017

(86) PCT No.: PCT/JP2017/008761
§ 371 (c)(1),
(2) Date: Feb. 28, 2019

(87) PCT Pub. No.: WO2018/042725
PCT Pub. Date: Mar. 8, 2018

(65) Prior Publication Data
US 2019/0194645 A1 Jun. 27, 2019

(30) Foreign Application Priority Data

Sep. 5, 2016 (JP) .............................. JP2016-172800

(51) Int. Cl.
*C12N 15/10* (2006.01)
*C12M 1/00* (2006.01)
*C12N 15/09* (2006.01)

(52) U.S. Cl.
CPC ......... *C12N 15/1013* (2013.01); *C12M 47/06* (2013.01); *C12N 15/09* (2013.01); *C12N 15/1006* (2013.01)

(58) Field of Classification Search
CPC .......................... C12N 15/1013; C12N 15/09; C12N 15/1003; C12N 15/1006; C12M 47/06
See application file for complete search history.

(56) References Cited

U.S. PATENT DOCUMENTS 8,357,530 B2    1/2013  Matsunaga et al.
10,030,240 B2   7/2018  Shirai et al.
(Continued)

FOREIGN PATENT DOCUMENTS

WO    2009/016842 A    2/2009
WO    2014/141386 A    9/2014
(Continued)

OTHER PUBLICATIONS

Vacuum filtration. 2007. pp. 1, as evidenced by the web page [retrieved on Mar. 17, 2021]. Retrieved from the Internet: <URL: http://www.chem.ucla.edu/~bacher/General/30BL/tips/vacuum>. (Year: 2007).*

(Continued)

*Primary Examiner* — Jehanne S Sitton
*Assistant Examiner* — Daniel W Nielsen
(74) *Attorney, Agent, or Firm* — Procopio, Cory, Hargreaves & Savitch LLP

(57) ABSTRACT

A device is provided for capturing a nucleic acid in a single cell, having: a two-dimensional array comprising a substrate, a plurality of single cell capturing holes provided on one surface of the substrate, and a nucleic acid capturing region comprising, on the inside of the substrate, a nucleic acid capturing body, which is configured to capture the nucleic acids extracted from the individual cells respectively captured by the single cell capturing hole; a flow channel which is provided adjacent to the nucleic acid capturing region of the substrate, and is configured to discharge a solution in the nucleic acid capturing region; and a cylindrical structure body which is arranged on the substrate at the time of introducing a cell suspension and encloses a plurality of the single cell capturing holes, wherein the cylindrical structure body is removed after the cells are captured by the single cell capturing holes.

8 Claims, 9 Drawing Sheets

(56) References Cited

U.S. PATENT DOCUMENTS

| | | | |
|---|---|---|---|
| 2007/0292941 A1* | 12/2007 | Handique | B01L 3/50273 |
| | | | 435/288.7 |
| 2010/0240041 A1 | 9/2010 | Matsunaga et al. | |
| 2015/0167063 A1* | 6/2015 | Shirai | C12N 15/1096 |
| | | | 506/9 |
| 2016/0010078 A1* | 1/2016 | Shirai | B01L 3/502761 |
| | | | 506/26 |
| 2017/0282180 A1 | 10/2017 | Yagi et al. | |

FOREIGN PATENT DOCUMENTS

| | | | | |
|---|---|---|---|---|
| WO | WO-2014141386 A1 * | 9/2014 | | B01L 7/52 |
| WO | 2016/031971 A | 3/2016 | | |

OTHER PUBLICATIONS

Jarvius, M. et al. "In Situ Detection of Phosphorylated Platelet-derived Growth Factor Receptor β Using a Generalized Proximity Ligation Method" Molecular & Cellular Proteomics, Jun. 12, 2007, 10 pages, vol. 6 iss. 9.

International Search Report for related International Application No. PCT/JP2017/008761, dated May 30, 2017; 1 page.

\* cited by examiner

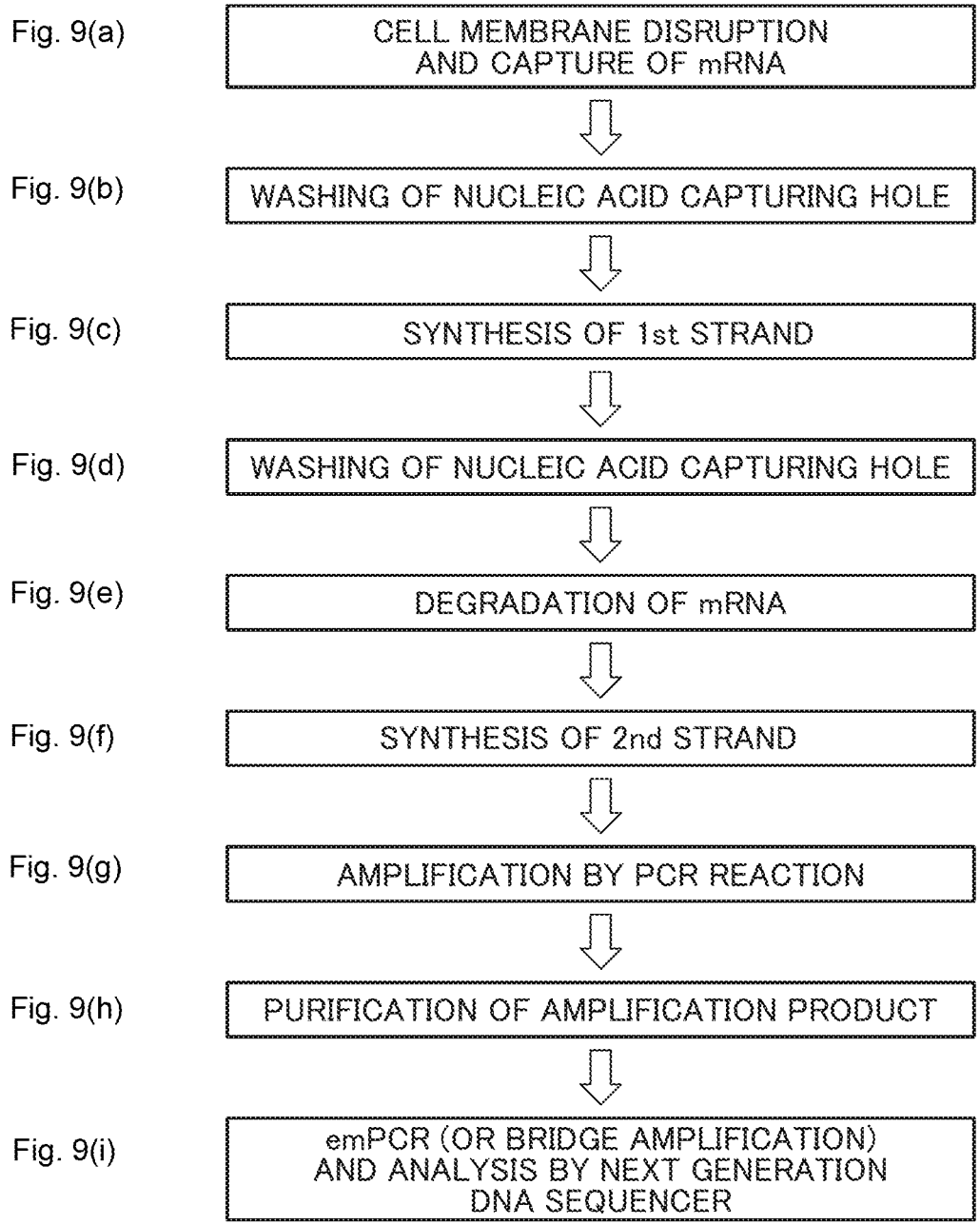

SYSTEM FOR ANALYZING SINGLE CELL

CROSS-REFERENCE TO RELATED APPLICATIONS

This application is a U.S. National Stage entry of PCT Application No: PCT/JP2017/008761 filed Mar. 6, 2017, which claims priority to Japanese Patent Application No. 2016-172800, filed Sep. 5, 2016, the contents of which are incorporated herein by reference.

TECHNICAL FIELD

The present invention relates to the fields of gene expression analysis, cell function analyses, analysis methods of biological tissues, diagnoses of diseases, drug discoveries, and the like. In detail, the present invention relates to a device and a method for capturing a nucleic acid (for example, mRNA) at a single cell level, and a system and a method for analyzing a nucleic acid at single cell level.

BACKGROUND ART

Recently, when performing genome analysis, gene expression analysis, and protein analysis of biological tissues made up from a large number of cells, the importance of an analysis which focuses on the differences in the genome, gene expression, or protein at the single cell level has begun to be recognized. In conventional analyses, DNA, RNA and protein which are biological molecules are extracted from a large number of cells sampled from biological tissues to perform the analyses, thus, an average analysis among the samples has been performed. Therefore, even if the quantity of the DNA, RNA, or protein in the individual cells deviated from the average value, it has been difficult to evaluate it. The single-cell analysis is important as an analysis method for solving such a problem of averaging.

Single-cell analysis is a technology which can detect or quantify the biological molecules in cells for each single cell at a high accuracy. In single cell analysis dealing with particularly mRNA as a biomolecule, the following steps are required: isolating the cells for individual treatment, efficiently extracting mRNAs to be measured in cells, synthesizing cDNA (reverse transcription), performing PCR amplification if necessary, and then conducting sequence analysis of the obtained product.

In a single-cell analysis, since the biological molecules (specifically, mRNA) contained in a single cell are in extremely small amounts, a capture method of biological molecules having a good efficiency is required. Further, as the gene expression levels of the individual cells randomly vary temporally and spatially, it is necessary to measure a large number of the individual cells in order to statistically extract the chemical and medical indicators as final data. Furthermore, as reagents such as enzymes used for analysis are often expensive, it is necessary to reduce the amount of reagents in order to reduce the analysis cost.

As a method for isolating cells in order to individually treat them, there is the technique which uses a filter in which a micromesh or a plurality of through holes is formed in the thickness direction as described in Patent Literature 1 or Patent Literature 2.

As a means for solving the problems, Patent Literature 3 discloses a device for single cell analysis including a cell capture section for capturing the individual cells, a nucleic acid capture section formed with beads or a porous membrane on which DNA for capturing the nucleic acids are immobilized, which is arranged under the cell capture section, and a flow channel which connects the two types of capture sections, wherein the cell capture section, the flow channel and the nucleic acid capture section are paired in the vertical direction, and a plurality of the pairs are arranged two-dimensionally.

CITATION LIST

Patent Literature

Patent Literature 1: WO 2009/016842 A
Patent Literature 2: WO 2016/031971 A
Patent Literature 3: WO 2014/141386 A

SUMMARY OF INVENTION

Technical Problem

In order to simultaneously perform a DNA sequence analysis or a gene expression analysis at a single cell level with a large number of cells and at a low cost, it is effective to use a device shown in Patent Literature 3 which uses the porous membrane on which the DNA for capturing the nucleic acid is immobilized on the inner wall or beads on which the nucleic acid capture DNA is immobilized which are arranged two-dimensionally.

FIG. 1 shows a schematic diagram of a device for a single-cell analysis described in Patent Literature 3. The device consists of a flat substrate 112, an upper reaction region 114 and a lower reaction region 115 which vertically sandwich the aforementioned flat substrate 112. In the aforementioned flat substrate 112, structures in which a cell capture section 110 and a nucleic acid capture section 111 are arranged vertically are arranged in an array.

By introducing a cell suspension to the upper reaction region 114 from a cell inlet 100 and sucking from a lower outlet 103, the cells are captured by the cell capture section 110. Next, a Lysis solution which is a cell membrane disruption solution is introduced from an upper inlet 101, the upper reaction region 114 is filled with the Lysis solution, the membrane of the cell captured by the cell capture section 110 is disrupted, and the nucleic acids within the cell are eluted. After the intracellular nucleic acids are eluted, a voltage is applied across the flat substrate, and the eluted nucleic acids are transferred by electrophoresis from the upper reaction region 114 to the lower reaction region 115. At this time, the eluted nucleic acids are captured by the nucleic acid capture section 111.

In Patent Literature 3, probes modified with different tag sequences for each cell capture section 110 are immobilized to the nucleic acid capture section 111. With this tag sequence, it is possible to distinguish a nucleic acid which was recovered from the cell capture section at the time of sequence analysis of the sample, thus, nucleic acid sequence analysis of individual single cells becomes possible. However, when introducing the cell suspension to the upper reaction region, cells may be nonspecifically adsorbed and remain on the inner walls 130, 131, 132 constituting the upper reaction region. If cells remain in areas other than the cell capture section, when the intracellular nucleic acids are eluted, the nucleic acids are also eluted from the residual cells, and are captured by a plurality of nucleic acid capture sections. If the nucleic acids eluted from one cell are captured by a plurality of nucleic acid capture sections, sequence analysis is performed with a composition different from that of the original nucleic acid composition, which may lead to a reduction in the analysis accuracy.

By coating the inner wall of the upper reaction region with bovine serum albumin (BSA) or a polymer such as polyethylene glycol chain, the nonspecific adsorption of the cells can be prevented, but it is desirable to more completely prevent the nonspecific adsorption.

The object of the present invention is to provide a means for reducing the cell adsorption region, in order to reduce the influence of the nucleic acids from cells other than the cell capture section when nucleic acids are simultaneously analyzed from a plurality of cells.

Solution to Problem

In order to solve the aforementioned problems, the device and system according to the present invention have the following configuration. Specifically, the device for capturing a nucleic acid in a single cell according to the present invention comprises: a two-dimensional array comprising a substrate, a plurality of single cell capturing holes provided on one surface of the substrate, and a nucleic acid capturing region comprising, on the inside of the substrate, a nucleic acid capturing body, which is configured to capture the nucleic acids extracted from the individual cells respectively captured by the single cell capturing hole; a flow channel which is provided adjacent to the nucleic acid capturing region of the substrate, and is configured to discharge a solution in the nucleic acid capturing region; and a cylindrical structure body which is arranged on the substrate at the time of introducing a cell suspension and encloses a plurality of the single cell capturing holes, wherein the cylindrical structure body is removed after the cells are captured by the single cell capturing holes.

Further, the system for analyzing a nucleic acid in a single cell according to the present invention comprises: a two-dimensional array comprising a substrate, a plurality of single cell capturing holes provided on one surface of the substrate, and a nucleic acid capturing region comprising, on the inside of the substrate, a nucleic acid capturing body, which is configured to capture the nucleic acids extracted from the individual cells respectively captured by the single cell capturing hole; a means for introducing a cell suspension to the surface of the substrate, on which the single cell capturing holes are provided; a flow channel which is provided adjacent to the nucleic acid capturing region of the substrate, and is configured to discharge a solution in the nucleic acid capturing region; a means for applying a negative pressure from the side opposite the side of the substrate, on which the single cell capturing holes are provided; a cylindrical structure body enclosing the plurality of single cell capturing holes; and a mechanism which is configured to arrange the cylindrical structure body on the substrate when introducing the cell suspension and to remove the cylindrical structure body after capturing the cells by the single cell capturing holes.

Advantageous Effects of Invention

According to the present invention, the adsorption of cells in regions other than the single cell capturing holes can be reduced and the influence of nucleic acids from cells other than the cells captured by the single cell capturing holes can be reduced when biological molecules (nucleic acid) are analyzed simultaneously from a plurality of cells. As a result, the device, the system and the method according to the present invention can efficiently and reliably capture nucleic acids in a single cell and can analyze the single cell-derived nucleic acids with a high accuracy, and are useful in the fields of gene expression analysis, cell function analyses, analysis methods of biological tissues, diagnoses of diseases, drug discoveries, and the like.

BRIEF DESCRIPTION OF DRAWINGS

FIGS. 8(a)-8(d), 8(c') and 8(d') shows the step of introducing the cell suspension to a device for capturing a nucleic acid in a single cell.

FIGS. 9(a)-9(i) shows the steps from mRNA capture in a single cell until the acquisition of a gene expression profile.

DESCRIPTION OF EMBODIMENTS

Figure 1:
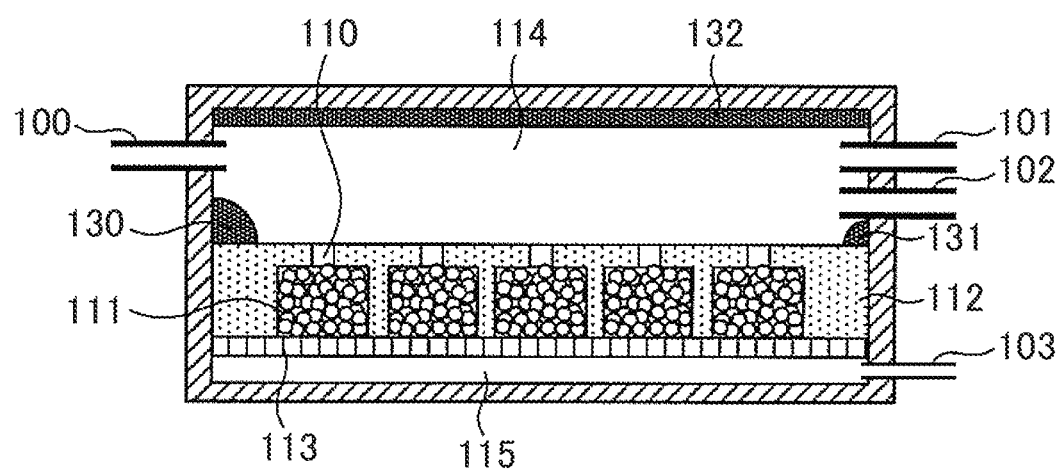
FIG. 1 shows a cross sectional diagram of a conventional device for capturing a nucleic acid in a single cell.

The present invention provides a device and a method for capturing efficiently and at a high accuracy the respective nucleic acids in a single cell from a sample containing a plurality of cells for the final purpose of preparing a library (for example, a cDNA library) of nucleic acids (for example, mRNA) from a biological tissue at a single cell level resolution, and conducting expression analysis of the nucleic acids at the single cell level resolution capability by a next generation DNA sequencer or hybridization which uses a probe specific to the gene to be analyzed.

According to the present invention, the term "nucleic acid in a single cell" refers to a nucleic acid which is a biological molecule contained within a single cell, and is a nucleic acid derived from the respective single cells in a sample (cell suspension) containing a plurality of cells. Similarly, the term "single cell level resolution capability" specifically means the ability to analyze a nucleic acid in a single cell for the respective single cells in a sample containing a plurality of cells.

According to the present invention, the term "capture of nucleic acids" means that the nucleic acid molecules contained within the cells are extracted to be separated from the other cell components, and means that such a nucleic acid molecule is preferably immobilized. Further, the term "gene expression analysis" means analyzing the nucleic acids related to gene expression, and specifically, quantitatively analyzing the nucleic acids in a sample (cells, tissue sections and the like), for example, the expression of the target nucleic acid to be tested, analyzing the expression distribution of the nucleic acids to be tested in a sample, and obtaining correlation data between a specific position and the expression level of the nucleic acids to be tested in a sample.

The nucleic acids to be captured or analyzed in the present invention are not specifically limited as long as they are nucleic acids contained in cells, and may include messenger RNA (mRNA), non-coding RNA (ncRNA), microRNA, genomic DNA, and fragments thereof.

In one aspect, the device (referred to as the "device for capturing a nucleic acid in a single cell") according to the present invention, for capturing a plurality of cells contained in a cell suspension, and extracting and capturing the nucleic acids from each of the captured single cells includes:

a two-dimensional array comprising a substrate, a plurality of single cell capturing holes provided on one surface of the substrate, and a nucleic acid capturing region comprising, on the inside of the substrate, a nucleic acid capturing body, which is configured to capture the nucleic acids extracted from the individual cells respectively captured by the single cell capturing hole;

a flow channel which is provided adjacent to the nucleic acid capturing region of the substrate, and is configured to discharge a solution in the nucleic acid capturing region; and a cylindrical structure body which is arranged on the substrate at the time of introducing a cell suspension and encloses a plurality of the single cell capturing holes, wherein the cylindrical structure body is removed after the cells are captured by the single cell capturing holes.

The two-dimensional array may be formed on the substrate, a plurality of single cell capturing holes are provided on one surface of the substrate, and a nucleic acid capturing region is provided in the substrate. This kind of two-dimensional array has been known in the technical field as described in Patent Literature 3 and the like.

For example, the substrate is not specifically limited as long as the substrate is prepared from a material which is generally used in the technical field. Examples of such a material include metals such as gold, silver, copper, aluminum, tungsten, molybdenum, chromium, platinum, titanium, and nickel; alloys such as stainless steel, Hastelloy, Inconel, Monel, and Duralumin; silicon; glass materials such as a glass, a quartz glass, a fused quartz, a synthetic quartz, an alumina, sapphire, ceramics, forsterite and a photosensitive glass; plastics such as polyester resin, polystyrene, a polyethylene resin, a polypropylene resin, an ABS resin (Acrylonitrile Butadiene Styrene resin), polydimethylsiloxane (PDMS), cyclic polyolefin, nylon, an acrylic resin, a fluororesin, a polycarbonate resin, a polyurethane resin, a methylpentene resin, a phenol resin, a melamine resin, an epoxy resin and a vinyl chloride resin; agarose, dextran, cellulose, polyvinyl alcohol, nitrocellulose, chitin, and chitosan. The materials used in the substrate may preferably be hydrophobic materials, and as a result, the adsorption of cells, reagents and the like can be reduced.

The method for providing the single cell capturing holes on one surface of a substrate, and providing a nucleic acid capturing region having the nucleic acid capturing body in the substrate is known. In order to increase the capture efficiency of nucleic acids, materials having a large surface area may preferably be used as the nucleic acid capturing region having the nucleic acid capturing body, for example, it is preferable to utilize a structure filled with a large number of beads, a porous structure, a mesh structure, or the like. When using beads as the nucleic acid capturing body, the beads can be prepared from resin materials (polystyrene and the like), oxides (glass and the like), metals (iron and the like), sepharose, and a combination thereof. From the ease of operation, magnetic beads are preferably used. A pore sheet or the like may be arranged so that this kind of nucleic acid capturing body does not leak out from the nucleic acid capturing region.

It is necessary that the size of the single cell capturing hole is smaller than the size of the cells to be captured, and has a size to the extent that a negative pressure can be applied to the surface of the substrate which will be described later. For example, the size may be 2 to 10 μm, and preferably 2 to 8 μm, but the size may be appropriately changed in accordance with the type of cell to be captured. The arrangement and the spacing of the single cell capturing holes on the substrate can also be appropriately changed in accordance with the type of cell to be captured, and in order to ensure and facilitate the capture of a single cell by each hole, the single cell capturing holes can be regularly arranged at a set interval, or can be arranged alternately.

The nucleic acid capturing body may contain an appropriate probe in accordance with the type of nucleic acid to be captured, preferably a probe which is specifically bound to a nucleic acid molecule. For example, when the nucleic acid is mRNA, a DNA probe containing a poly T sequence can be used. The DNA probe containing a poly T sequence, i.e., the oligo (dT) can be synthesized by a conventional method, and the polymerization degree of the oligo (dT) may be a polymerization degree such that the DNA probe can hybridize with the poly A sequence of the mRNA and can capture the mRNA in a nucleic acid capturing body on which the oligo (dT) is immobilized. For example, the probe may be made to a range of 10 to 30 bases, 10 to 20 bases, or 10 to 15 bases. When the nucleic acid is a non-coding RNA (ncRNA), microRNA or genomic DNA, a DNA probe consisting of random sequences or a DNA probe having a sequence complementary to a specific target sequence can be used. Further, as another method, when the object is to capture a biological molecule such as a protein or a low molecular weight compound in place of the nucleic acid, a first binding molecule (antibody, aptamer and the like) which is specifically bound to these biological molecules can be utilized with a first DNA probe bound to the first binding molecule. When a second binding molecule (which is preferably the same type of molecule as the aforementioned first binding molecule, and is, for example, an antibody, an aptamer and the like) which is bound to the aforementioned biological molecule in a state sandwiched with the aforementioned first binding molecule is added with a second DNA probe bound to the second binding molecule, and the target biological molecule is present, the aforementioned DNA probe is ligated with the second DNA probe, and a ring probe specific to the biological molecule is formed. This method is referred to as the Proximity Ligation Method (for example, Malin Jarvius et al. Molecular & Cellular Proteomics 6 (9) p. 1500, 2007), and is useful for constructing a DNA library corresponding to the protein.

The probe may be immobilized onto a nucleic acid capturing body in accordance with any method known in the art. For example, the probe can be immobilized to the bead surface, the surface or the inside of the porous membrane by use of covalent bonding, ion bonding, physical adsorption or biological binding (for example, binding of biotin and avidin or streptoavidin, antigen-antibody binding or the like). Further, it is possible to immobilize the probe to the nucleic acid capturing body via a spacer sequence. When a protein or a low molecular weight compound is treated as the biological molecule using the Proximity Ligation method, it is possible to immobilize the first binding molecule to the capture body.

The surface may preferably be coated so that the other substances (nucleic acids and proteins and the like) are not adsorbed to the two-dimensional array and the substrate.

A flow channel is also known in the technical field, and may be integrally provided with the substrate or the two-dimensional array, or maybe connected after being prepared separately as long as they are adjacent to the nucleic acid capturing region. The solution of the nucleic acid capturing region may be discharged from this flow channel.

The cylindrical structure body is a configuration having a size and a shape which encloses the plurality of single cell capturing holes. The shape of the cylindrical structure body is not particularly limited as long as it is cylindrical (a shape which is rod-like and having a hollow center), and when viewed from the upper surface, can be made to a shape such as a rectangle (FIG. 7(b)), a rounded rectangle, a circle, an ellipse or a triangle. From the ease of the introduction of the cell suspension, it is preferable that the cross-section of the cylindrical structure body is a tapered shape (the upper part is wide and the lower part is narrow). Regarding the size of the cylindrical structure body, the inner diameter of the cylinder is a size in the range which can enclose all of the single cell capturing holes. In order to reduce the possibility that the cells are adsorbed to the surface of the substrate instead of in the single cell capturing holes, it is preferable that the size be the minimum size capable of enclosing all of the single cell capturing holes. Further, the length of the cylinder may be adjusted corresponding to the height of the reaction region on the substrate. The material of the cylindrical structure body is not specifically limited, and a material used in the preparation of the substrate, for example, a polypropylene resin can be similarly used, and is preferably a hydrophobic material, whereby the adsorption of cells and the like can be reduced.

When the cylindrical structure body is arranged on the substrate, the device according to the present invention, preferably has a further means for controlling the distance between the surface of the substrate, on which the single cell capturing holes are provided, and the end of the cylindrical structure body. As a result, breakage of the substrate or the problem of cell capture due to negative pressure application can be avoided. For example, this means can be a fixing tool provided in the cylindrical structure body, for example, a projection, and it is possible to immobilize the cylindrical structure body to a predetermined position on the substrate with the fixing tool. In addition or alternatively, this means can be a mechanism which is configured to control the movement of the cylindrical structure body, for example, a vertical drive mechanism. This mechanism may be useful for the removal of the cylindrical structure body.

The cylindrical structure body may be arranged on the substrate when introducing the cell suspension, or may be arranged on the substrate in advance. The cylindrical structure body is arranged so as to enclose the plurality of single cell capturing holes provided on the substrate. This cylindrical structure body is removed after the cells are captured by the single cell capturing holes, after the introduction of the cell suspension.

The device of the present invention having the aforementioned configuration is provided with a cylindrical structure body, thus, it is easy to remove the cells not captured in the single cell capturing holes but adsorbed on the cylindrical structure body, the adsorption of cells in a reaction region other than the capturing hole can be reduced, and the influence in which the nucleic acids (mRNA and the like) eluted from these types of adsorbed cells are mixed in the nucleic acid capturing region can be reduced. Specifically, it is possible to reliably capture the nucleic acids derived from a single cell in separate nucleic acid capturing regions from the sample (cell suspension) containing a plurality of cells.

In another aspect, the system for analyzing a nucleic acid in a single cell according to the present invention includes:

a two-dimensional array comprising a substrate, a plurality of single cell capturing holes provided on one surface of the substrate, and a nucleic acid capturing region comprising, on the inside of the substrate, a nucleic acid capturing body, which is configured to capture the nucleic acids extracted from the individual cells respectively captured by the single cell capturing hole;

a means for introducing a cell suspension to the surface of the substrate, on which the single cell capturing holes are provided;

a flow channel which is provided adjacent to the nucleic acid capturing region of the substrate, and is configured to discharge a solution in the nucleic acid capturing region;

a means for applying a negative pressure from the side opposite the side of the substrate, on which the single cell capturing holes are provided;

a cylindrical structure body enclosing the plurality of single cell capturing holes; and a mechanism which is configured to arrange the cylindrical structure body on the substrate when introducing the cell suspension and to remove the cylindrical structure body after capturing the cells by the single cell capturing holes.

The means for introducing the cell suspension is well-known in the technical field, and is not specifically limited. For example, a storage dispenser which is configured to store and dispense a cell suspension can be used. Further, this means may include a means (for example, a dispensing pressurizer and the like) for controlling the amount of the cell suspension to be dispensed. It is possible to further reduce the cells adsorbed on the inner wall of the cylindrical structure body or the reaction region by using this means to control the dispensing so that the cell suspension does not come into contact with a surface other than the substrate as much as possible (FIGS. 8(c') and (d')).

The means for applying a negative pressure is well-known in the technical field, and for example, a syringe, a pump, a suction device and the like can be used. By applying a negative pressure from the side opposite the side of the substrate on which the single cell capturing holes are provided, the capturing of cells by the single cell capturing holes can be performed. Moreover, if the application of the negative pressure is continued, the washing of the substrate or the two-dimensional array can be performed while maintaining the cells captured by the single cell capturing holes as is, and/or the capturing of nucleic acids in the nucleic acid capturing region can be performed efficiently and without crosstalk.

The system for analyzing a nucleic acid in a single cell according to the present invention may further include a reagent introducing means, a temperature control means, an optical observation means, a movement stage and the like.

The system of the present invention having the aforementioned configuration is provided with a cylindrical structure body, thus, it is easy to remove the cells not captured in the single cell capturing holes but adsorbed on the cylindrical structure body, the adsorption of cells in a reaction region other than the capturing hole can be reduced, and the influence in which the nucleic acids (mRNA and the like) eluted from these types of adsorbed cells are mixed in the nucleic acid capturing region can be reduced. Specifically, it is possible to reliably capture the nucleic acids derived from a single cell in the separate nucleic acid capturing regions from a sample (cell suspension) containing a plurality of cells.

Further, in another aspect, the method for capturing a nucleic acid in each of a single cell from a cell suspension (sample) containing a plurality of cells (referred to as the "method of capturing a nucleic acid in a single cell") according to the present invention includes:

preparing the aforementioned device or system according to the present invention;

introducing the cell suspension to the cylindrical structure body in a state in which the cylindrical structure body is arranged on the substrate;

applying a negative pressure from the side opposite the side of the substrate, on which the single cell capturing holes are provided to capture the cells by the single cell capturing holes;

removing the cylindrical structure body; and lysing the captured cell, and capturing the nucleic acid by the nucleic acid capturing body.

The cell suspension (sample) is not specifically limited as long as it is a sample containing a plurality of cells. The organism from which the sample is derived is not particularly limited, and a sample derived from any organism, such as a vertebrate (for example, a mammal, a bird, a reptile, a fish, an amphibian and the like), an invertebrate (for example, an insect, a nematode, a crustacean and the like), a protist, a plant, a fungus, a bacterium, and a virus may be used. It is necessary that the cell suspension (sample) is in a form which flows through the flow channel when used in the device, the system or the method according to the present invention. Therefore, when the initial form is a solid sample (for example, a tissue section and the like), it is preferable to prepare the cell suspension by lysing or suspending the solid sample in a solvent. Further, when the initial form is a gas sample (for example, air, breath and the like), it is preferable to prepare the cell suspension by suspending the cells contained in the gas sample in a solvent. The preparation methods of the cell suspension have been commonly used in the technical field, and can be easily understood by a person skilled in the art.

The cell suspension containing the plurality of cells to be measured is introduced to the cylindrical structure body in a state in which the cylindrical structure body is arranged on the substrate. In this case, it is preferable to control the dispensing amount of the cell suspension in order to prevent the cells from adsorbing on the inner wall of the cylindrical structure body or the reaction region. Subsequently, by applying a negative pressure from the side opposite the side of the substrate, on which the single cell capturing holes are provided, the plurality of cells contained in the cell suspension may be captured by the single cell capturing holes one by one. Next, the cylindrical structure body is removed to remove the cells adsorbed on the inner wall of the cylindrical structure body.

When necessary, a suitable solvent, a buffer solution and the like are made to flow and introduced to a surface of the substrate, and the two-dimensional array is washed. The cells may be captured by the single cell capturing holes as is, and the unnecessary cells and components adsorbed on the substrate can be washed.

Then, a reagent for cell lysis is introduced to lyse the captured cells, and capture the nucleic acids by the nucleic acid capturing body of the two-dimensional array. For example, a reagent for cell lysis known in the technical field may be used to lyse the cells, and the nucleic acids contained in the cells can be extracted. For example, a proteolytic enzyme such as Proteinase K, a chaotropic salt such as guanidine thiocyanate and guanidine hydrochloride, a surfactant such as Tween and SDS, or a commercially available reagent for cell lysis can be used to lyse the cells, and the nucleic acids contained therein, i.e., the DNA and RNA can be eluted. When the nucleic acid captured is mRNA, only the RNA may be captured after the DNA is degraded with a DNA nuclease (DNase).

By using the device or system according to the present invention, it is possible for the method of capturing a nucleic acid in a single cell according to the present invention to capture only a single cell by the individual single cell capturing holes from a sample (cell suspension) containing a plurality of cells, and to efficiently and reliably capture single cell-derived nucleic acids from the captured cell.

Specific embodiments of the present invention will be described below with reference to the drawings.

Example 1

In the present example, a device and a system having the configuration of the present invention for capturing a nucleic acid as a biological molecule in a single cell from a plurality of cells as the sample and analyzing the gene expression analysis will be explained.

Figure 2A:
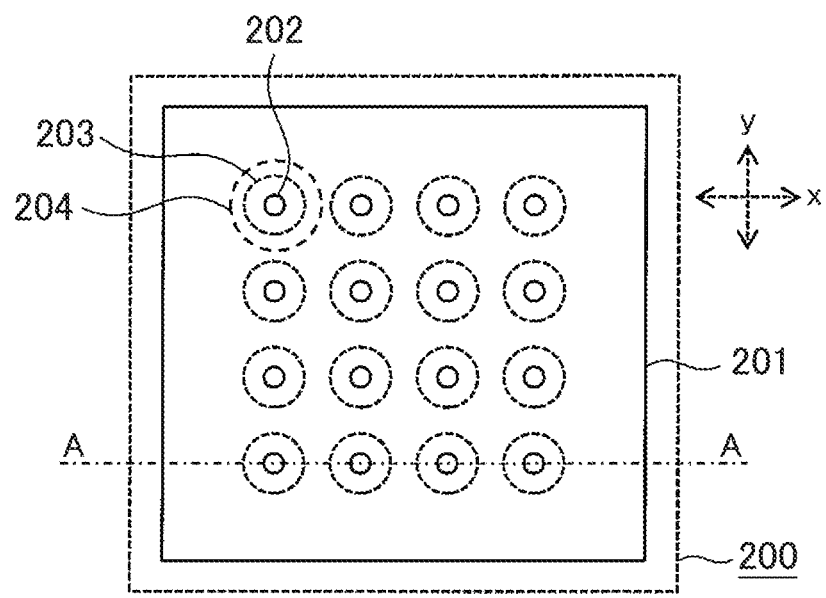
FIGS. 2(a) and 2(b) show a schematic diagram of one example of a chip for capturing a nucleic acid in a single cell.
Figure 2B:
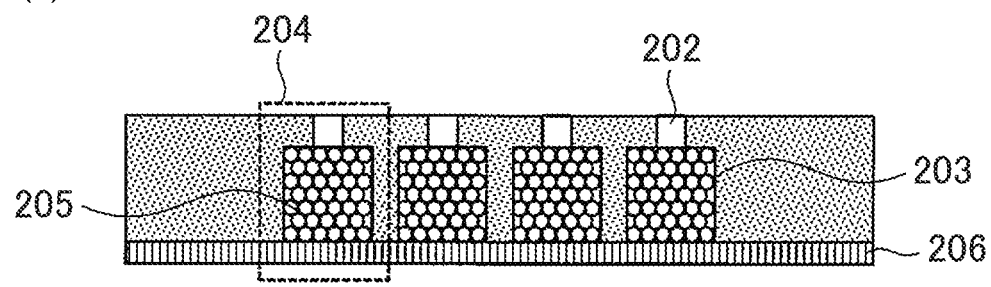

FIG. 2 shows a schematic diagram of a chip for capturing a nucleic acid in a single cell 200. FIG. 2(a) shows the plan view of the chip for capturing a nucleic acid in a single cell 200 and FIG. 2(b) shows an A-A section view of FIG. 2(a) chip for capturing a nucleic acid in a single cell 200. A chip for capturing a nucleic acid in a single cell 200 has a structure in which a capture vessel 204 in which the single cell capturing hole 202 and the nucleic acid capturing hole 203 are arranged vertically was arranged in a two-dimensional array in the substrate 201 made of polydimethylsiloxane (PDMS) formed by injection molding and laser processing. The capture vessels 204 are arranged at 200 μm intervals in the xy direction, and a total of 16 capture vessel 204 are arranged in one chip for capturing a nucleic acid in a single cell 200.

In one capture vessel, the single cell capturing holes 202 are provided in the upper part of FIG. 2(b) and the nucleic acid capturing holes 203 are provided in the lower part of FIG. 2(b). Magnetic beads 205 having a diameter of 1 μm are filled in the nucleic acid capturing holes 203. The diameter of the opening of the single cell capturing hole 202 was made to 3 μm and the diameter of the opening of nucleic acid capturing holes 203 was made to 70 μm. A pore sheet 206 made of alumina having an opening in the range of 500 nm was arranged so that the magnetic beads 205 do not leak from the lower part of FIG. 2(b). The PDMS substrate 201 was adhered with the pore sheet 206 by plasma adhesion. Here, the resin chips obtained by injection molding using other resins (polycarbonate, cyclic polyolefin, polypropylene and the like) may be used in place of the PDMS substrate 201, or the resin chips obtained using a nano imprinting technique or a semiconductor process may be used. Further, magnetic beads are used in the present example, but other than this, the beads can be prepared from resin materials (polystyrene and the like), oxides (glass and the like), metals (iron and the like), sepharose, and combinations thereof.

Figure 3:
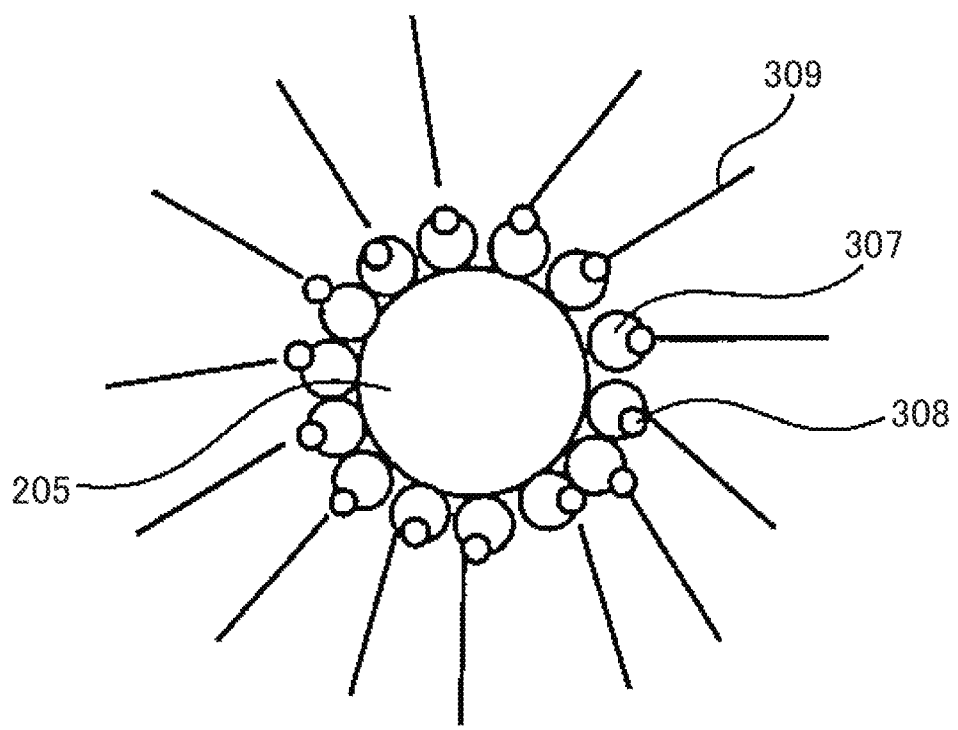
FIG. 3 shows a schematic diagram of the magnetic beads.

FIG. 3 shows a schematic diagram of the magnetic beads 205 for capturing nucleic acids. A large amount of streptavidin 307 is modified around the magnetic beads 205, and a probe 309 for capturing nucleic acids in which biotin 308 is bound to the 5' end via the streptavidin 307 is bound.

Figure 4:
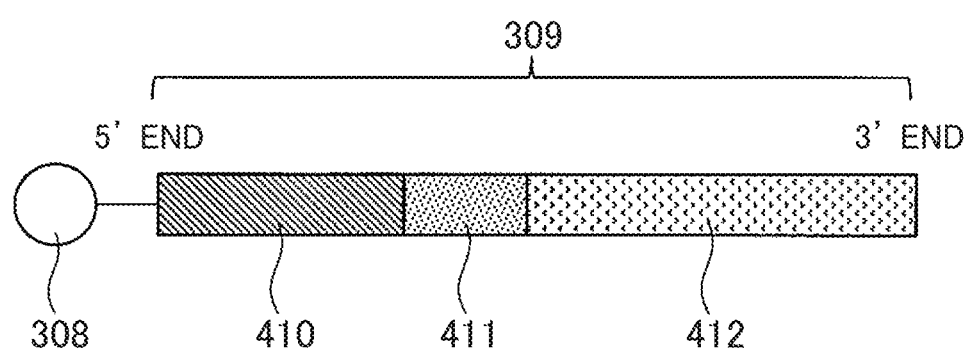
FIG. 4 shows a schematic diagram of a probe for capturing the nucleic acid.

FIG. 4 shows a schematic diagram of an example of the probe for capturing the nucleic acids 309. The probe for capturing the nucleic acids 309 in which the biotin 308 is bound to the 5' end consists of a common sequence for PCR amplification (Forward) 410, a cell recognition tag sequence 411 and a nucleic acid capture sequence 412 in order from the 5' end. Here, the oligo (dT) was used as the nucleic acid capture sequence. By using the oligo (dT), it is possible to hybridize with the poly A sequence of mRNA and capture the mRNA from the sample cell. The polymerization degree of the oligo (dT) may be a polymerization degree such that the oligo (dT) hybridizes with the poly A sequence of mRNA and captures the mRNA on the magnetic beads 205 on which the probe containing the oligo (dT) is immobilized. For example, the probe may be made to a range of 10 to 30 bases, 10 to 20 bases, or 10 to 15 bases. Further, the nucleic acid to be captured in the present example is mRNA, but, for example, when the nucleic acid to be captured is a microRNA or genomic DNA, a random sequence, or a sequence complimentary to a part of a target nucleic acid to be tested can be used as the nucleic acid capture sequence. By introducing the common sequence for PCR amplification 410 into the probe for capturing the nucleic acids 309, this sequence can be utilized as a common primer in the subsequent PCR amplification step. Further, it is desirable that the cell recognition tag sequence 411 has a different sequence by each nucleic acid capturing hole. When the number of bases constituting the cell recognition tag sequence 411 is 5 bases, $4^5=1024$ positions or regions (for example $4^5=1024$ single cells) can be recognized, and it becomes possible to recognize which cell (or the position or the region) the finally obtained sequence data of the next generation sequencer is derived from. This tag sequence has been described in detail in Patent Literature 3.

Figure 5A:
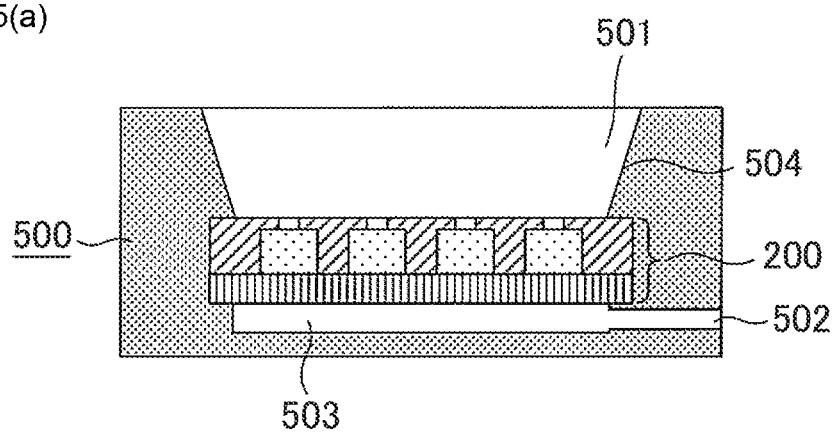
FIGS. 5(a) and 5(b) show a schematic diagram of one example of the device for capturing a nucleic acid in a single cell.
Figure 5B:
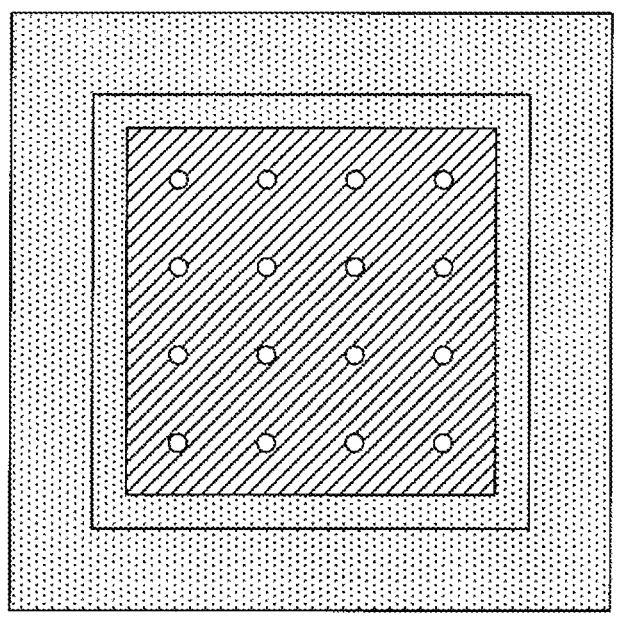

FIG. 5 shows a schematic diagram of an example of the device for capturing a nucleic acid in a single cell 500 incorporated in a chip for capturing a nucleic acid in a single cell 200. FIG. 5(a) shows a cross-sectional drawing and FIG. 5(b) shows a plan view. The device for capturing a nucleic acid in a single cell 500 is constituted from an upper reaction region 501 which introduces the cell suspension, the reagent and the washing buffer, a suction port 502 which sucks and discharges the solution, a lower reaction region 503, and an inner wall 504. Acrylic resin is used as the material of the device for capturing a nucleic acid in a single cell 500 in the present example, but the material may also be a metal or a resin other than acrylic resin. However, it is preferable to avoid materials that inhibit nucleic acid capturing or the cDNA synthesis reaction. For example, aluminum and the like should be avoided as they inhibit the cDNA synthesis reaction. In order to reduce the dead volume of the cell suspension, the reagent and the washing buffer, it is desirable that the upper reaction region 501 is positioned directly above the chip for capturing a nucleic acid in a single cell 200.

Figure 6:
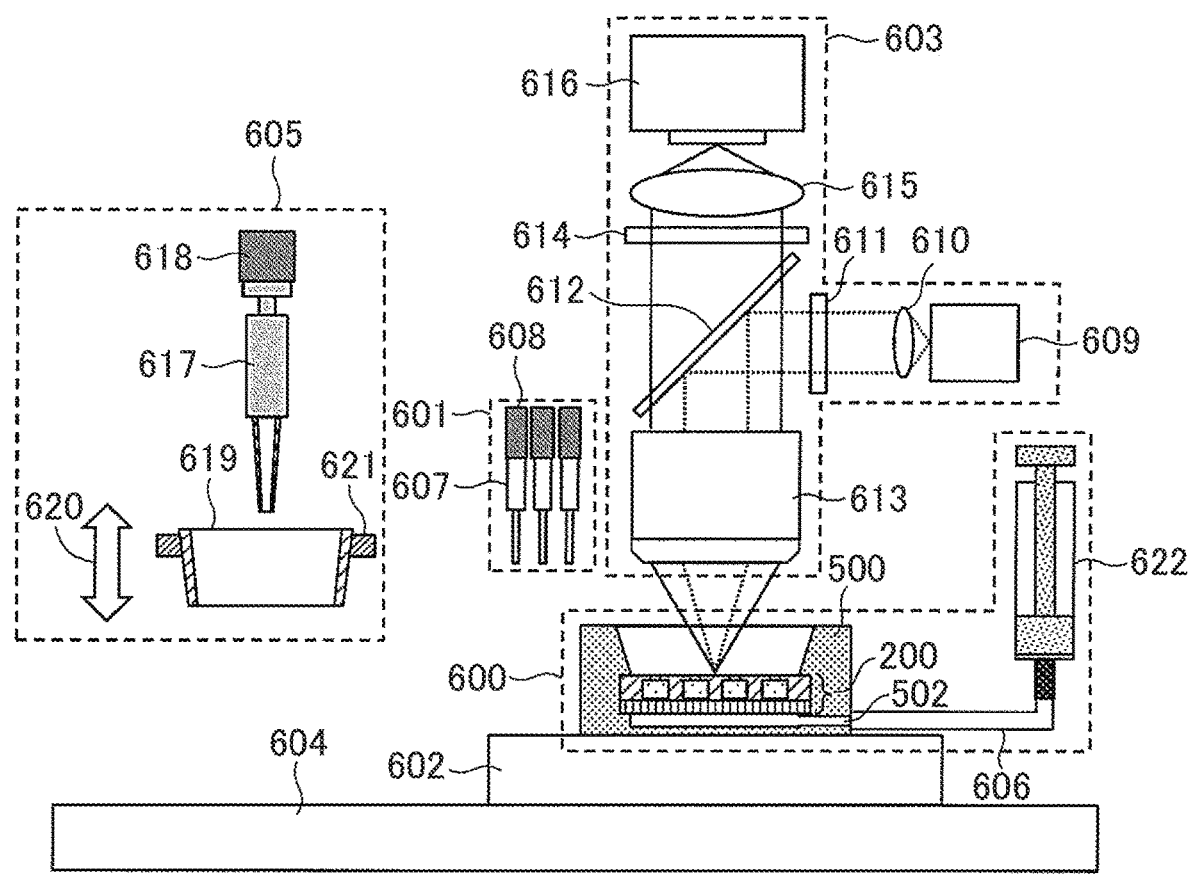
FIG. 6 shows a schematic diagram of one example of the system for analyzing a nucleic acid in a single cell.

FIG. 6 shows a schematic diagram of an example of the system for analyzing a nucleic acid in a single cell. The system for analyzing a nucleic acid in a single cell is constituted from a liquid feeding unit 600 including the device for capturing a nucleic acid in a single cell, a reagent dispensing unit 601, a temperature adjustment unit 602 which is configured to perform the temperature adjustment of the device for capturing a nucleic acid in a single cell, an optical observation unit 603 which is configured to perform the optical observation of the chip for capturing a nucleic acid in a single cell 200, a movement stage unit 604 which is configured to move the device for capturing a nucleic acid in a single cell 500 to the desired position, and a sample dispensing unit 605 which is configured to introduce the cell suspension.

The liquid feeding unit 600 is constituted as follows. A syringe 622 is connected via a suction tube 606 made of PEEK to the suction port 502 of the device for capturing a nucleic acid in a single cell. It becomes possible to apply a negative pressure to the chip for capturing a nucleic acid in a single cell 200 by the syringe 622, and thus, suck the solution on the single cell capturing hole surface.

The reagent dispensing unit 601 is constituted by a reagent storage dispenser 607 which is configured to store and dispense the reagent and the washing buffer, and a dispensing pressurizer 608 which is configured to pressurize the reagent storage dispenser 607 at a specific time in order to dispense the reagent and the washing buffer. The reagent storage dispenser 607 is constituted from a polypropylene resin and a glass capillary, and if pressurized at a constant pressure and time from the upper part of a polypropylene resin storage part in which the reagent and the washing buffer are stored, the reagent and the washing buffer are dispensed from the tip of the capillary. It is possible for each reagent storage dispenser 607 to be separately pressurized. In the present example, the temperature of the reagent storage dispenser 607 is not adjusted, but the temperature may be adjusted (specifically, to a low temperature (4° C. and the like)) in order to prevent the deterioration of the reagent.

The temperature adjustment unit 602 may adjust the temperature within the device for capturing a nucleic acid in a single cell 500 from 4° C. to 85° C., and thus, is constituted from the combination of a Peltier and a heater. More specifically, the temperature adjustment unit 602 has high thermal conductivity metal (for example, copper). The metal was adhered to the surface of Peltier element with high thermal conductivity adhesive and was embedded heater inside. The metal was connected to the device for capturing a nucleic acid in a single cell 500 via a thermally conductive sheet.

The optical observation unit 603 is constituted from a light source 609 using a halogen lamp to excite a fluorophore GFP (Ex/Em=488/507 nm) labelled on the cell which is the sample to be described later, a condensing lens 610, an optical filter 611, a dichroic mirror 612, an objective lens 613, an optical filter 614, an imaging lens 615, and a CCD camera 616. The light from the light source 609 is converted into a parallel light beam by the condensing lens 610, excludes the wavelengths in the vicinity of 480 nm by the optical filter 611 which is a band pass filter having a central wavelength of 480 nm, is reflected by the dichroic mirror 612 which reflects wavelengths of 500 nm or less, is collected by the objective lens 613, and is irradiated on the cell captured in the chip for capturing a nucleic acid in a single cell 200 within the device for capturing a nucleic acid in a single cell 500. The fluorescence from the irradiated cell is collected by the objective lens 613, passes through the dichroic mirror 612, excludes the background light by the optical filter 614 which cuts the wavelengths of 500 nm or less, and is imaged on the CCD camera 616 by the imaging lens 615. In the present example, the configuration of an epi illumination-style fluorescence microscope is used, but may also be the configuration of an epi-illumination style bright field or dark field microscope for directly observing the cell.

The movement stage unit 604 is configured from an automatic movement stage, and the temperature adjustment unit 602 and the device for capturing a nucleic acid in a single cell 500 are arranged on the movement stage. The movement stage and the temperature adjustment unit 602 are connected to each other via a thermal insulation material so as to not be influenced by the temperature of the temperature adjustment unit 602. The movement stage unit 604 makes it possible to move the device for capturing a nucleic acid in a single cell 500 to a position which can dispense the reagent from the reagent dispenser 607, a position which can dispense the sample from the sample dispensing unit 605, or a position which uses the optical observation unit 603 to measure the cell.

The sample dispensing unit 605 is constituted from a sample dispenser 617, a dispensing pressurizer 618 which is configured to pressurize the sample dispenser 617 for a specific time in order to dispense the sample, and a dispenser cover 619. The cell suspension which is the sample is stored in the sample dispenser 617, and if the dispensing pressurizer 618 is pressurized at a constant pressure and time by the upper part of the sample dispenser 617, the cell suspension is dispensed from the sample dispenser end. A vertical drive mechanism 620 which raises and lowers the dispenser cover itself is connected to the dispenser cover 619.

Figure 7A:
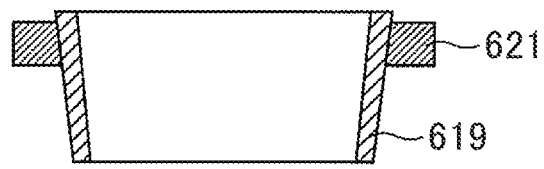
FIGS. 7(a)-7(c) show a schematic diagram of a dispenser cover and the state in which the dispenser cover is arranged in the device for capturing a nucleic acid in a single cell.
Figure 7B:
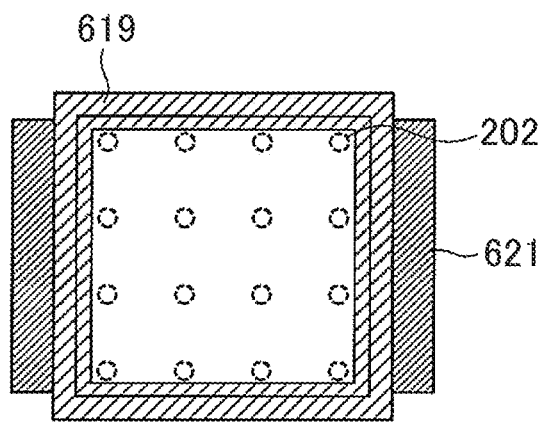
Figure 7C:
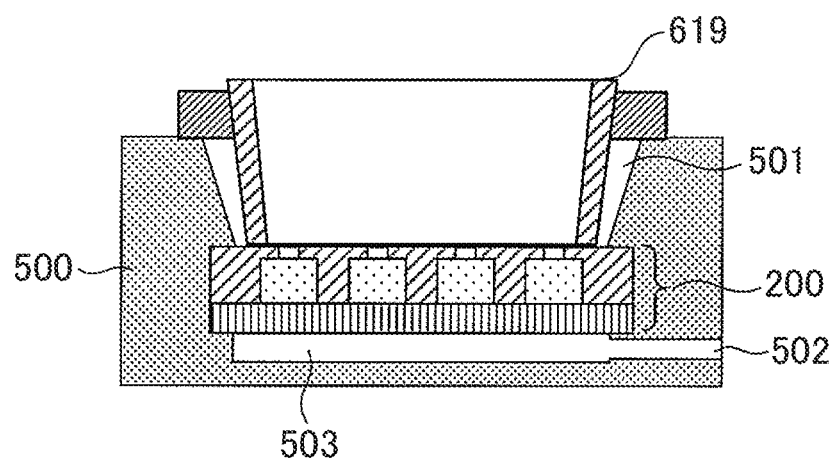

FIG. 7 shows a schematic diagram of the dispenser cover 619. FIG. 7(a) shows a cross-sectional drawing and FIG. 7(b) shows a top view. FIG. 7(c) shows the state in which the dispenser cover is arranged in the device for capturing a nucleic acid in a single cell. The top view of FIG. 7(b) shows the positional relationship of the single cell capturing holes 202 when introducing the cell suspension to the device for capturing a nucleic acid in a single cell 500. The shape of a dispenser cover 619 is a cylindrical shape obtained by cutting the tip of a polypropylene resin quadrangular pyramid. A projection 621 is arranged at a predetermined height from a pointed end of the dispenser cover. The larger the size of the inside of the pointed end of the dispenser cover 619, the greater the possibility that the cell is adsorbed onto the surface other than the single cell capturing holes of the chip for capturing a nucleic acid in a single cell 200. Therefore, it is desirable that the inside of the pointed end of the dispenser cover 619 is the minimum size at which all of the single cell capturing holes can be contained.

Example 2

In the present example, the procedures for using the device and the system having the configuration of the present invention to capture each cell from the cell suspension containing the plurality of cells which are the sample is explained.

The step of introducing the cell suspension 823 which is the sample to the device for capturing a nucleic acid in a single cell 500 is shown in FIG. 8. First, around 20 or fewer cells were washed in 500 μL of 1×PBS without damaging the cells, the solution was removed so that as little as possible PBS remained, and the cell suspension to which 10 μL of 1×PBS buffer was added was prepared. The fluorophore GFP had been incorporated into the cell beforehand.

The cell suspension 823 is filled in the sample dispenser 617. The device for capturing a nucleic acid in a single cell 500 is moved directly below the dispenser cover 619 by the movement stage unit 604. The dispenser cover 619 is brought into contact with the upper part of the chip for capturing a nucleic acid in a single cell 200 by a vertical drive mechanism 620 (FIG. 8(a)). At this time, breakage due to the excessive insertion of the end of the dispenser cover 619 into the upper surface of the chip for capturing a nucleic acid in a single cell 200 can be prevented by the upper surface of the device for capturing a nucleic acid in a single cell 500 being in contact with the projection 621. It is desirable that the end of the dispenser cover 619 is brought into contact with the upper surface of the chip for capturing a nucleic acid in a single cell 200, but there may be some gaps as long as the cell suspension does not leak out from the gaps between the end of dispenser cover 619 and the upper surface of the chip for capturing a nucleic acid in a single cell 200. The distance between the end of the dispenser cover 619 and the upper surface of the chip for capturing a nucleic acid in a single cell 200 was controlled by the projection 621, but the distance may be controlled by moving only a predetermined distance by the vertical drive mechanism 620.

Alternatively, the dispenser cover 619 may be set in the device for capturing a nucleic acid in a single cell 500 in advance (for example, the state shown in FIG. 7(c)). In this case, the procedures (FIG. 8(a)) for arranging the dispenser cover can be omitted.

Figure 8A:
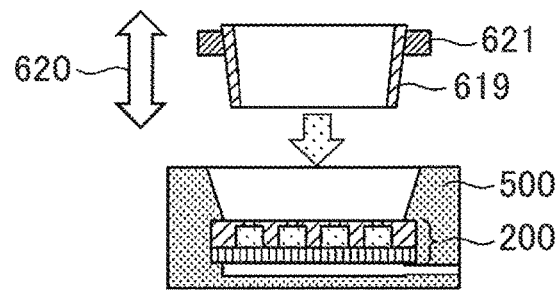
Figure 8B:
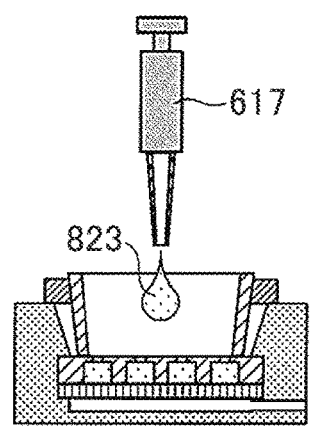
Figure 8C:
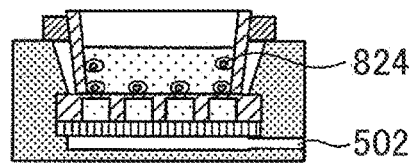
Figure 8C:
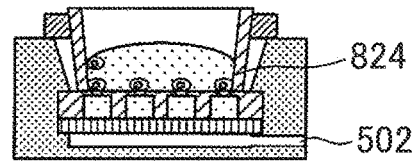
Figure 8D:
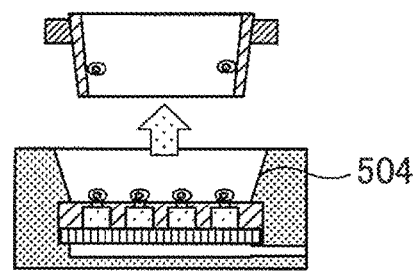
Figure 8D:
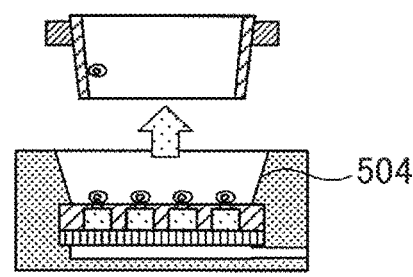

After the dispenser cover 619 end comes into contact with the upper surface of the chip for capturing a nucleic acid in a single cell 200, pressure is applied from the dispensing pressurizer 618, and the cell suspension 823 is added from the sample dispenser 617 to the inside of the dispenser cover 619 (FIG. 8(b)). At this time, it is further preferable to control the amount (dispensing amount) of the cell suspension 823 to be introduced because of reduction of the cells adsorbed on the dispenser cover 619 or the inner wall of the upper reaction region (FIG. 8(c')). After the injection of the cell suspension 823, a suction operation is performed by sucking with the syringe 622 from the suction port 502, and the cell suspension is sucked within the chip for capturing a nucleic acid in a single cell 200 (FIGS. 8(c) and (c')). The size of the cell 824 is in the range of 10 thus, the cell 824 cannot pass through the single cell capturing hole 202, and is captured by the aforementioned capturing hole. The suction operation is performed until a state in which almost none of the cell suspension remains on the upper surface of the chip for capturing a nucleic acid in a single cell 200. Next, the dispenser cover 619 is raised by the vertical drive mechanism 620, and removed from the device for capturing a nucleic acid in a single cell 500 (FIGS. 8(d) and (d')). By the cell suspension introducing method, adsorption of cells to the inner wall 504 of the device for capturing a nucleic acid in a single cell 500 can be suppressed.

Next, the device for capturing a nucleic acid in a single cell is moved directly below the optical observation unit 603 by the movement stage unit 604. The cell is labelled with the fluorophore GFP (Ex/Em=488/507 nm) beforehand, thus, it can be verified as to which single cell capturing hole the cell was captured within by fluorescence observation using the optical observation unit 603. In order to observe the cell aspiration situation, it is necessary to remove the dispenser cover 619 from the vertical drive unit 620 after the cell suspension added to the inside of the dispenser cover 619, move the device for capturing a nucleic acid in a single cell 500 directly below the optical observation unit 603 by the movement stage unit 604, and perform the suction operation. When performing the observation, the focus is shifted due to the suction operation changing the height of the cell suspension surface, thus, it is necessary to adjust the distance between the objective lens 613 and the device for capturing a nucleic acid in a single cell 500 by the movement stage unit 604 in accordance with the change in the liquid surface height.

By use of the dispenser cover 619, the adsorption of cells in regions other than the single cell capturing holes can be reduced, it is possible to more completely capture a single cell by the single cell capturing hole, and the nucleic acids derived from a single cell can be accurately captured in the nucleic acid capturing region.

Example 3

In the present example, the method for using the device or the system having the configuration of the present invention to capture nucleic acids as biological molecules in a single cell from the captured cells, and perform gene expression analysis at a single cell level resolution is explained.

The steps from the capture of the intracellular mRNA to acquisition of a gene expression profile by a next generation (large scale) sequencer will be explained. As shown in FIG. 9, the main steps include the cell membrane disruption and the capturing of the mRNA (FIG. 9(a)), the washing of the nucleic acid capturing hole (FIG. 9(b)), the synthesis of the $1^{st}$ strand (cDNA) (FIG. 9(c)), the washing of the nucleic acid capturing hole (FIG. 9(d)), the degradation of the mRNA (FIG. 9(e)), the synthesis of the $2^{nd}$ strand (FIG. 9(f)), the amplification by a PCR reaction (FIG. 9(g)), the purification of the amplification product (FIG. 9(h)), and emPCR (or bridge amplification) and the analysis by a next generation DNA sequencer (FIG. 9(i)).

More specifically, the following steps are performed. The device for capturing a nucleic acid in a single cell 500 is moved by the movement stage unit 604 directly below the reagent storage dispenser 607 in which the Lysis solution adjusted with 39.5 µL of Real-time ready Lysis buffer (Roche), 39.5 µL of Protector (Roche), and 0.5 µL of Protector RNase Inhibitor (Roche) is filled, the dispensing pressurizer 608 pressurizes the reagent storage dispenser 607 at a predetermined pressure and time, and the Lysis solution is introduced to the device for capturing a nucleic acid in a single cell 500. The suction operation (negative pressure application) is performed by pulling the syringe 622 to generate a flow perpendicular to the chip for capturing a nucleic acid in a single cell 200, and the Lysis solution pass through each capture vessel 204 of the chip for capturing a nucleic acid in a single cell 200. The cell is lysed by the Lysis solution, and the mRNA in the cell is eluted. The eluted mRNA continues to flow from the single cell capturing holes 202 towards the nucleic acid capturing hole 203 by the flow generated by the suction operation perpendicular to the chip for capturing a nucleic acid in a single cell 200. In this process, the mRNA is captured in the oligo (dT) portion which is the nucleic acid capture sequence 412 of the probe for capturing the nucleic acids 309 immobilized to the magnetic beads 205 (FIG. 9(a)).

Next, the device for capturing a nucleic acid in a single cell 500 is moved by the movement stage unit 604 directly below the reagent storage dispenser 607 in which 1×PBS buffer which is the washing buffer is filled, the dispensing pressurizer 608 pressurizes the reagent storage dispenser 607 at a predetermined pressure and time, and the washing buffer is introduced to the device for capturing a nucleic acid in a single cell 500. The suction operation is performed by pulling the syringe 622, the nucleic acid capturing hole 203 is washed, and the Lysis solution and the biological material other than the mRNA are washed away (FIG. 9(b)).

The device for capturing a nucleic acid in a single cell 500 is moved by the movement stage unit 604 directly below the reagent storage dispenser 607 in which a reverse transcription solution in which a mixture of 4 µL of 5×First strand buffer (Invitrogen Corporation), 4 µL of 10 mM dNTP (Invitrogen Corporation), 4 µL of Super Script III (reverse transcription enzyme, Invitrogen Corporation), and 4 µL of RNaseOUT (Invitrogen Corporation) is filled, the dispensing pressurizer 608 pressurizes the reagent storage dispenser 607 at a predetermined pressure and time, and the $1^{st}$ strand synthesis reagent is introduced to the device for capturing a nucleic acid in a single cell 500. The suction operation (negative pressure application) is performed by pulling the syringe 622 to generate a flow perpendicular to the chip for capturing a nucleic acid in a single cell 200, and the solution pass through each capture vessel 204 of the chip for capturing a nucleic acid in a single cell 200. The solution suction operation was stopped by the syringe 622 in a state in which the solution still remained on the upper surface of the chip for capturing a nucleic acid in a single cell 200, and after the temperature inside the device for capturing a nucleic acid in a single cell 500 was increased to 37° C. by the temperature adjustment unit 602 and left standing for ten minutes, the temperature was increased to 50° C. and maintained for 45 minutes to complete the reverse transcription reaction, whereby the 1st strand DNA (cDNA) having a complementary sequence to the mRNA was synthesized (FIG. 9(c)).

After the cDNA strand was synthesized, the reverse transcription enzyme was inactivated by raising the temperature inside the device for capturing a nucleic acid in a single cell 500 to 85° C. by the temperature adjustment unit 602 and maintaining for ninety seconds. After inactivation of the reverse transcription enzyme, the temperature inside the device for capturing a nucleic acid in a single cell 500 is cooled to 4° C., and then, the device for capturing a nucleic acid in a single cell 500 is moved by the movement stage unit 604 directly below the reagent storage dispenser 607 in which 1×PBS buffer which is the washing buffer is filled, the dispensing pressurizer 608 pressurizes the reagent storage dispenser 607 at a predetermined pressure and time, and the washing buffer is introduced to the device for capturing a nucleic acid in a single cell 500. The suction operation (negative pressure application) is performed by pulling the syringe 622 to generate a flow perpendicular to the chip for capturing a nucleic acid in a single cell 200, the solution pass through each capture vessel 204 of the chip for capturing a nucleic acid in a single cell 200, and the nucleic acid capturing holes 203 are washed (FIG. 9(d)).

The washed chip for capturing a nucleic acid in a single cell 200 was removed from the device for capturing a nucleic acid in a single cell 500, and inserting into resin tubes ((e.g., a 0.2 ml or 1.5 ml tube that is generally used). An RNaseH solution in which 1 µL of RNaseH (Invitrogen Corporation) was mixed with 1 µL of 10×RNaseH buffer (Invitrogen Corporation) was introduced into the respective tubes, and leaving the tube standing at 37° C. for thirty minutes, thereby degrading mRNA (FIG. 9(e)).

After mRNA degradation, 50 µL of Tris-tween buffer (10 mM Tris-HCl, pH 8.0, 0.1% Tween solution) was introduced into the tube; in order to wash the chip for capturing a nucleic acid in a single cell 200, and only the magnetic beads 205 were leaved in the tube using a magnet and were re-suspended with 1 µL of the Tris-tween buffer. The synthesis of the 2nd strand was carried out by adding 10 µL of the 2nd strand synthesis reagent mixed with 1 µL of 10×Platinum buffer, 1 µL of 2.5 mM dNTPs, 0.4 µL of 50 mM $MgSO_4$, 2.5 µL of each 10 µm gene-specific sequence primer, 0.1 µL of Platinum Taq H.F., 5 µL of sterile water to the tube and performing the reaction in the sequence of 98° C. for ten seconds, 43° C. for one minute, 68° C. for three minutes in a PCR device (FIG. 9(f)). In the present example, the DNA probes having the gene-specific sequences of 20 types (ATP5B, GAPDH, GUSB, HMBS, HPRT1, RPL4, RPLP1, RPS18, RPL13A, RPS20, ALDOA, B2M, EFF1Q SDHA, TBP, VIM, RPLP0, RPLP2, RPLP27, and OAZ1) to which a common sequence for PCR amplification (Reverse) has been added were used as the gene-specific sequence primers. The 20±5 bases in the region 109±8-bases upstream from the poly A tail of the target gene were used as the gene-specific sequence.

A magnet is brought into proximity of the tube in which the 2$^{nd}$ strand synthesis is performed and maintained at 4° C., and the 2nd strand synthesis reagent is removed so as to be in a state in which the only the magnetic beads 205 remain within the tube. Next, the magnetic beads were washed twice with 50 µL of Tris tween buffer while maintaining the tube at 4° C. and in close proximity to the magnet, and finally the beads were suspended in 1 µL of Tris tween buffer. After the washing process, 14.3 µL of PCR reagent to which 7 µL of Gflex (TaKaRa), 2 µL of a primer having a common sequence for PCR amplification (Forward), 2 µL of a primer having a common sequence for PCR amplification (Reverse), 0.3 µL of Gflex polymerase (TaKaRa), and 3 µL of sterile water are introduced in the tube. The tube was maintained for thirty seconds at 94° C., and then the PCR amplification step was performed by subjecting the tube to the following three-step cycle: 94° C. for thirty seconds→55° C. for thirty seconds→68° C. for thirty seconds. The cycle was repeated 40 times. Finally, after maintaining at 68° C. for three minutes, the tubes were cooled to 4° C. (FIG. 9(g)). By the above step, the target portion of the 20 types of target genes are amplified, but the sizes of all the PCR products are nearly uniform at 200±8 bases.

After the PCR reaction, the amplification product amplified by the step is purified using PCR Purification (Qiagen) for the purpose of removing the free common sequence primer for PCR amplification and residual reagents such as the enzymes contained in the solution (FIG. 9(h)). After the purified solution is subjected to emPCR amplification or bridge amplification, an analysis is performed by subjecting the amplification product to a next generation DNA sequencer of the respective companies (Life Technologies (Solid/Ion Torrent), Illumina (High Seq) etc.) (FIG. 9(i)).

The non-specific adsorption of the cells in a region other than the single cell capturing holes can be reduced by the present example, thus, the influence of the mRNA eluted from the non-specific adsorption cell can be reduced, and the analysis accuracy can be improved.

In the present example, the steps following the mRNA degradation (FIG. 9(e)) were performed by transferring the chip for capturing a nucleic acid in a single cell 200 to a separate tube, but the steps until the amplification by the PCR reaction of FIG. 9(g) may be performed in the device for capturing a nucleic acid in a single cell 500, and the reaction liquid from the device for capturing a nucleic acid in a single cell may be recovered in order to perform the reaction in a separate tube after the purification of the amplification product FIG. 9(h).

LIST OF REFERENCE SIGNS

100 Cell Inlet
101 Upper Inlet
102 Upper Outlet
103 Lower Outlet
110 Cell Capture Section
111 Nucleic Acid Capture Section
112 Flat Substrate
113 Flow Channel
114 Upper Reaction Region
115 Lower Reaction Region
130 Inner Wall (Cell Adsorption Region)
131 Inner Wall (Cell Adsorption Region)
132 Inner Wall (Cell Adsorption Region)
200 Chip for Capturing a Nucleic Acid in a Single Cell
201 Substrate
202 Single Cell Capturing Hole
203 Nucleic Acid Capturing Hole
204 Capture Vessel
205 Magnetic Beads
206 Pore Sheet
307 Streptavidin
308 Biotin
309 Probe for Capturing Nucleic Acids
410 Common Sequence for PCR Amplification
411 Cell Recognition Tag Sequence
412 Nucleic Acid Capture Sequence
500 Device for Capturing a Nucleic Acid in a Single Cell
501 Upper Reaction Region
502 Suction Port
503 Lower Reaction Region
504 Inner Wall
600 Liquid Feeding Unit
601 Reagent Dispensing Unit
602 Temperature Adjustment Unit
603 Optical Observation Unit
604 Movement Stage Unit
605 Sample Dispensing Unit
606 Suction Tube
607 Reagent Storage Dispenser
608 Dispensing Pressurizer
609 Light Source
610 Condensing Lens
611 Optical Filter
612 Dichroic Mirror
613 Objective Lens
614 Optical Filter
615 Imaging Lens
616 CCD Camera
617 Sample Dispenser
618 Dispensing Pressurizer
619 Dispenser Cover
620 Vertical Drive Mechanism
621 Projection
622 Syringe
823 Cell Suspension
824 Cell

The invention claimed is:

1. A method for capturing a nucleic acid in each of a plurality of single cells from a cell suspension comprising a plurality of cells, comprising:
(i) preparing a system for analyzing a nucleic acid in a single cell, the system comprising: a two-dimensional array comprising a substrate, a plurality of single cell capturing holes provided on an upper surface of the substrate, and a nucleic acid capturing region comprising, on an inside of the substrate, a nucleic acid capturing body, which is configured to capture the nucleic acids extracted from individual cells respectively captured by the single cell capturing hole; a means for introducing a cell suspension to the upper surface of the substrate, on which the single cell capturing holes are provided; a flow channel which is provided adjacent to the nucleic acid capturing region of the substrate, and is configured to discharge a solution in the nucleic acid capturing region; a means for applying a negative pressure from the surface opposite the upper surface of the substrate on which the single cell capturing holes are provided; a cylindrical structure body enclosing the plurality of single cell capturing holes; and a mechanism which is configured to arrange the cylindrical structure body on the upper surface of the substrate when introducing the cell suspension by bringing the cylindrical structure body into contact with the upper surface of the substrate and to remove the cylindrical structure body after capturing the cells by the single cell capturing holes;

(ii) introducing the cell suspension to the cylindrical structure body in a state in which the cylindrical structure body is arranged on the upper surface of the substrate;

(iii) applying a negative pressure from the surface opposite the upper surface of the substrate on which the single cell capturing holes are provided to capture the cells by the single cell capturing holes;

(iv) removing the cylindrical structure body; and (v) lysing the captured cell, and capturing the nucleic acid by the nucleic acid capturing body.

2. The method of claim 1, wherein when the cylindrical structure body is arranged on the upper surface of the substrate, the system further comprises a means for controlling a distance between the upper surface on which the single cell capturing holes of the substrate are provided and an end of the cylindrical structure body.

3. The method of claim 2, wherein the means for controlling the distance is a fixing tool provided in the cylindrical structure body.

4. The method of claim 2, wherein the means for controlling the distance is a mechanism which is configured to control movement of the cylindrical structure body.

5. The method of claim 1, wherein the nucleic acid is mRNA.

6. The method of claim 1, wherein the nucleic acid capturing body is magnetic beads.

7. The method of claim 1, wherein when the cylindrical structure body is arranged on the upper surface of the substrate, the mechanism is configured to control a distance between the upper surface of the substrate, on which the single cell capturing holes are provided, and an end of the cylindrical structure body, or when the cylindrical structure body is arranged on the upper surface of the substrate, the cylindrical structure body has a fixing tool for controlling the distance between the upper surface on which the single cell capturing holes of the substrate are provided and the end of the cylindrical structure body.

8. The method of claim 1, wherein the means for introducing the cell suspension is provided with a means for controlling an amount of the cell suspension to be dispensed.

* * * * *